United States Patent [19]

Savoyet

[11] Patent Number: 4,608,864

[45] Date of Patent: Sep. 2, 1986

[54] DEVICE FOR SAMPLING AND MEASURING THE FLOW RATE OF A CONTINUOUSLY OR INTERMITTENTLY CIRCULATING LIQUID

[76] Inventor: Jean-Louis Savoyet, La Mayrie, F-38770 La Motte D'Aveillans, France

[21] Appl. No.: 625,469

[22] Filed: Jun. 28, 1984

[30] Foreign Application Priority Data

Jun. 30, 1983 [FR] France ................................ 83 11121

[51] Int. Cl.⁴ ............................ G01F 5/00; G01N 1/20
[52] U.S. Cl. ..................................... 73/202; 73/863.52; 119/14.17
[58] Field of Search ........... 73/863.41, 863.43, 863.51, 73/863.52, 202, 864.91; 119/14.17, 14.15, 14.16

[56] References Cited

U.S. PATENT DOCUMENTS

| | | | |
|---|---|---|---|
| 2,917,926 | 12/1959 | Jaquith | 73/863.51 |
| 3,481,197 | 12/1969 | Wenham | 73/202 |
| 3,512,411 | 5/1970 | Seaborne | 73/202 |
| 3,600,944 | 8/1971 | Hutchings | 73/863.51 |
| 4,213,341 | 7/1980 | Wenham | 73/863.43 |

FOREIGN PATENT DOCUMENTS 0057816  1/1982  European Pat. Off. .

Primary Examiner—Donald O. Woodiel
Attorney, Agent, or Firm—Michael N. Meller

[57] ABSTRACT

A device for sampling and measuring the flow rate of a continuously or intermittently circulating liquid, more particularly a foaming liquid, such as milk, comprises means for taking a sample of the liquid in proportions which are accurate and constant over time, a container for the sample thus taken and electric means for measuring the volume of the sample directly in the container. The sampling means comprise a cylindrical chamber into which the liquid is admitted via an inverted funnel-shaped head and distributed uniformly over a conical surface arranged at a small distance from the head, one or more lateral openings provided in the wall of the cylindrical chamber and opening into the container, and finally at least one opening for discharging the liquid.

14 Claims, 4 Drawing Figures

DEVICE FOR SAMPLING AND MEASURING THE FLOW RATE OF A CONTINUOUSLY OR INTERMITTENTLY CIRCULATING LIQUID

FIELD OF THE INVENTION

The present invention relates to a device for sampling and measuring the flow rate of a continuously or intermittently circulating liquid which can be applied particularly well to foaming liquids, such as milk.

BACKGROUND OF THE INVENTION

Devices of this type, in particular for measuring milk, are known which enable a sample to be taken, the volume of which is substantially proportional to the flow rate. This sample is then analyzed so as to pay the farmer according to the quantity and quality of the milk.

A device of this type is described, for example, in French Pat. No. 1,424,746, but this device suffers two sorts of defect. Firstly, it has to be operated in a perfectly level position so that the factor of proportionality between the flow rate and the volume of the sample taken is constant. It is widely acknowledged that this is a condition which is difficult to meet in a cow shed.

Moreover, as the volume of the sample is determined by reading the depth, it will be understood that this reading cannot be made accurately. In fact, freshly milked milk is a foaming liquid which does not have a clearly defined surface.

BRIEF SUMMARY OF THE INVENTION

The device according to the invention solves the foregoing problems while remaining simple and easy to operate, even in situ. This device comprises an inlet and an outlet for the liquid, means for taking a sample of the liquid in precise proportions which are constant over time, a container for the sample thus taken and electrical means for measuring the volume of the sample directly in the container.

According to a first embodiment, the sampling means comprise a chamber in which the liquid is admitted and distributed over a dome-shaped convex surface which constitutes the base of the chamber, means for distributing the flow of the liquid uniformly over the convex surface, at least one substantially vertical opening arranged regularly in the space, allowing a constant and given proportion of the liquid to be taken and opening into the container, and finally at least one opening for discharging the liquid.

There are advantageously three openings arranged at 120° to each other.

According to a second embodiment, the sampling means comprise a cylindrical chamber in which the liquid is admitted via an inverted funnel-shaped head and distributed uniformly over a conical surface arranged at a small distance from the head, at least one lateral opening made in the wall of the cylindrical chamber permitting a constant and given proportion of liquid to be taken and opening into the container, and finally at least one opening for discharging the liquid.

It is advantageous if the openings are arranged laterally and immediately below the conical surface and the axis thereof is preferably substantially parallel to this surface. A liquid film of constant thickness is formed over the entire surface. The lateral openings thus permit proportional sampling of liquid.

The conical surface is preferably fixed axially on elastic return means, for example a spring, acting against the sinking of this surface into the cylindrical chamber.

It is preferable for the cylindrical chamber to be surrounded by another cylindrical chamber, the annular space between the two chambers serving to receive the portion of sampled liquid for measurement and, if necessary, to admit a liquid for cleaning the container.

The electrical means are able to measure the weight of the liquid column present in the container, for example, by means of a pressure sensor, the slight deformations of which cause a variable electrical signal depending on the amplitude of these deformations.

The electrical means can also measure the dielectric constant of the liquid present in the container by means of a central anode extending vertically from the base of the container, the second electrode being constituted by the peripheral wall of the container or by a lining placed thereon. A capacitor of variable capacitance is thus produced.

The measured volume is preferably displayed directly, the electrical signal having been processed by a calculating logic unit.

According to a particularly advantageous embodiment, the device is integrated into an automated assembly permitting the sample to be poured outside the container and permitting the entire device to be cleaned and rinsed. In addition to the inlet and outlet circuits of the liquid, a circuit for emptying the container and a circuit for cleaning and rinsing are provided. These circuits are preferably constituted by flexible tubes and are controlled by valves acting directly on the tubes. A logic unit controls the valves and the opening and closing sequence thereof.

To simplify the description, the device will be described more particularly in its application to fresh milk, but it should be understood that it can be applied to any other foaming liquid and, more particularly, to any non-foaming liquid. Included are, for example, beer, natural petroleum or petroleum charged with surface-active agents for the recovery thereof, etc.

DETAILED DESCRIPTION OF THE DRAWINGS

Figure 1:
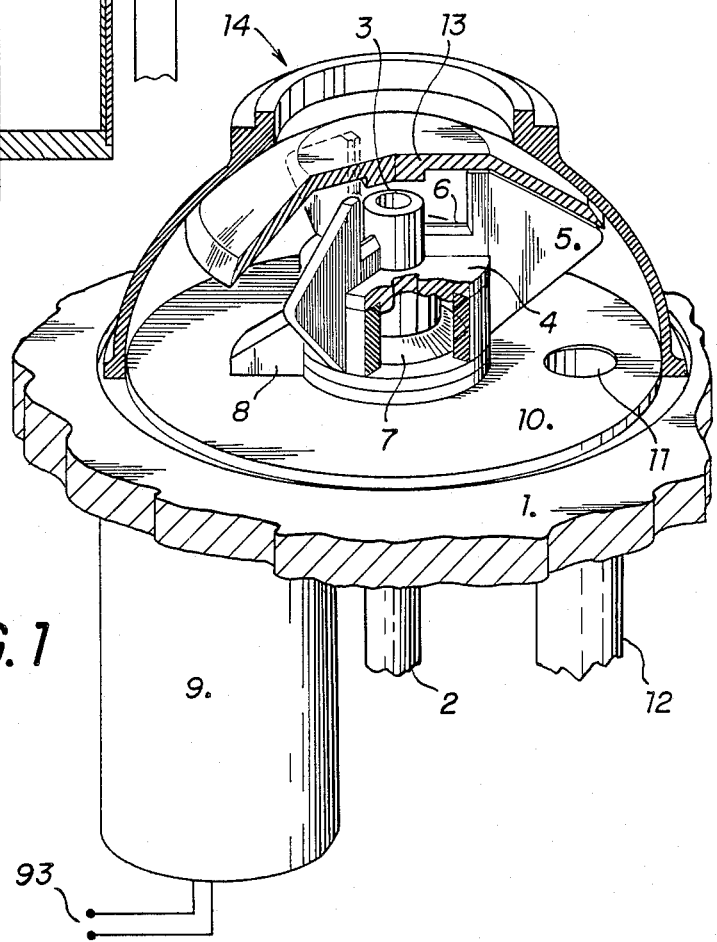
FIG. 1 is a partially cut away perspective view from above of a fresh milk sampling means in a first embodiment and of the container.

FIG. 1 shows the device with its base plate 1 serving to support the entire unit. An inlet tube 2 brings the milk to an outlet opening 3 from which it flows over a dome-shaped surface 4. The actual sampling means are constituted by blades 5 provided with fine slots 6 opening into a chamber 7.

A portion of the milk is taken through these slots 6 before flowing over the dome 4 and falling into the chamber 7 from which it flows into the container 9 via a tube 8.

The unsampled milk flows over the dome 4 and is then collected in a chamber 10 and passes via the outlet opening 11 into the outlet tube 12.

Means for uniformly distributing the flow of liquid towards the dome 4 are constituted by an obstacle 13 situated at a small distance from the inlet opening 3. Finally, the assembly is sealed by a cover 14 resting on the support 1.

There are three blades 5 evenly arranged at 120° to one another. It can thus be understood that the tilting of the device does not significantly affect sampling since the quantity sampled by the "lower" blades compensates for the quantity sampled by the "upper" blades.

Figure 2:
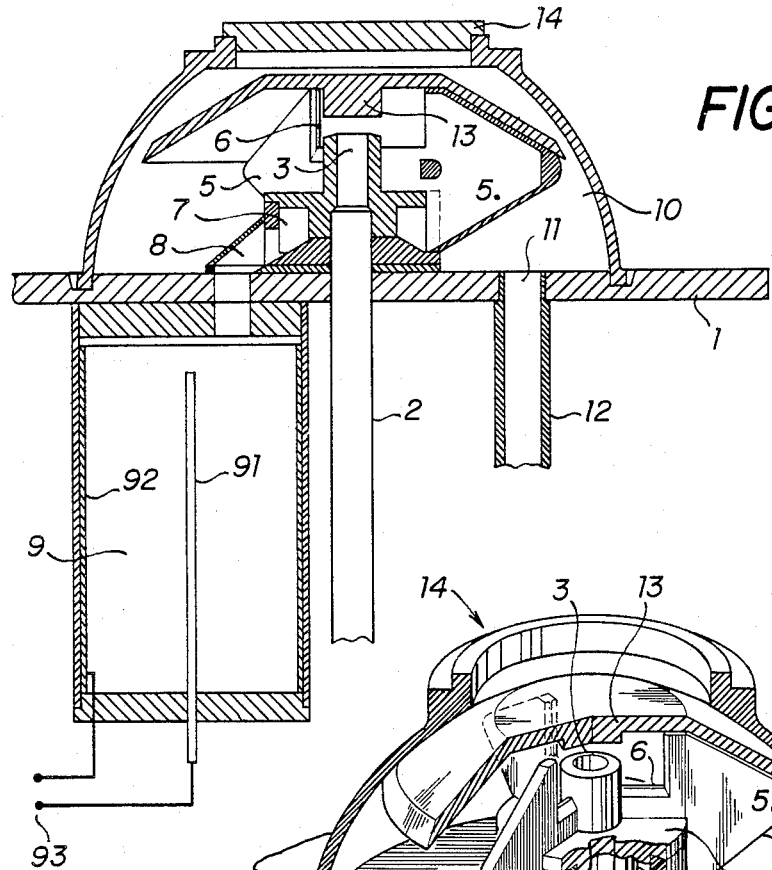
FIG. 2 is a sectional view of this device, the means for measuring the depth of the sample in the container being of the dielectric type.

As shown in FIG. 1, and even better in FIG. 2, the container 9 has a central anode 91, and the peripheral wall thereof is covered with a conductive lining 92, the electric circuit being placed in position 93.

This position 93 is connected to a calculating logic unit which deduces from the dielectric measurement the depth of the milk in the container 9 and therefore its volume.

The calculating means are preferably connected to display means, so that the volume of milk sampled can be obtained merely by reading.

As a variant, calculating and memory means may also be provided which enable the information to be stored and statistical calculations to be made, per cow milked, per farmer or per biotope.

In another embodiment, the electrodes 91 and 92 of the container 9 are replaced by a pressure sensor embedded in the base and measuring the pressure exerted thereon by the column of liquid. The slight deformations produce an electric signal which varies as a function of the amplitude of these deformations, this signal being processed by a logic unit to supply the volume of the sample taken.

Figure 3:
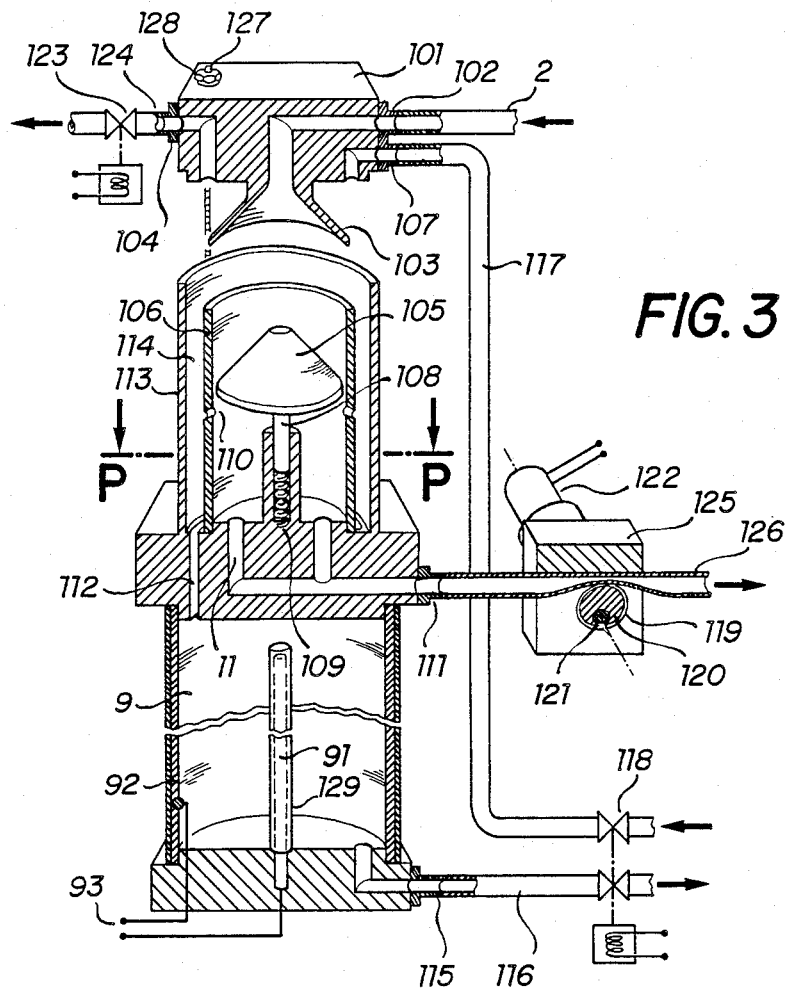
FIG. 3 is a sectional perspective view of the sampling means in a second embodiment, shown completely with the control valves thereof.

FIG. 3, which illustrates the second embodiment, shows a head 101 for admitting the milk via tube 102 which ends in an inverted funnel shape 103. A cleaning tube 104 as well as an air inlet tube 107 can also be seen.

The head 101 acts as a cover and is accommodated at the level of the funnel 103 in a cylindrical chamber 106 just above a conical surface 105 so that the milk admitted is distributed uniformly. This conical surface 105 is extended along its axis by a holding rod 108 resting in a housing on a spring 109.

The pressure of the milk admitted counterbalances the effect of the return spring 109 so that sufficient space is maintained between the funnel 103 and the conical surface 105. As a variation, the spring can be omitted and the shaft supporting the cone may or may not still be moveable.

In the walls of the cylindrical chamber 106 there are provided some lateral openings 110, the axis of which is substantially parallel to that of the conical surface 105 and which are arranged just beneath it.

The unsampled milk, that is to say the milk which does not pass through the lateral openings 110, is collected through the discharge openings 11 which meet in an outlet tube 111.

Figure 4:
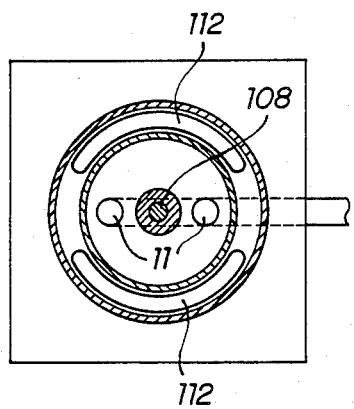
FIG. 4 shows a detailed view of FIG. 3 at the level of the plane P—P.

The sampled milk passes into the oblong holes 112 illustrated in detail in FIG. 4 and is collected in the container 9. In a variant which is not illustrated, the oblong holes can be replaced by one or more tubes.

It will be seen that the cylindrical chamber 106 is surrounded by another cylindrical chamber 113, defining an annular space 114 through which a liquid for cleaning or rinsing the container 9 passes, this liquid being admitted via the tube 104. A tube 115 serves to empty the container 9.

The tubes 104, 111 and 115 are provided with flexible hoses 124, 126 and 116 respectively, thus permitting pinching. It is advantageous if the complete device has three valves, the valve 125 controlling the outlet of the milk, the double valve 118 controlling the emptying of the container 9 and the valve 123 permitting cleaning.

The valves are closed by means of a reduction motor 122 and a shaft 121 which performs a quarter turn or a half turn causing a cam 120 to rotate. Pinching is thus effected as shown in FIG. 3.

It can be seen that the cam 120 is provided with a ring 119 which can cause elastic pinching and prevents tearing and damage of the flexible hose 126.

During the milking operation, the valve 125 is open and the valves 118 and 123 are closed. The milk arriving through the tube 102 flows over the cone 105, a portion thereof is taken via the lateral openings 110, as explained above, and flows into the container 9 via the openings 112. The other portion flows through the openings 11 into the tube 111.

After the milking operation the valve 125 can be closed and the double valve 118 is opened, thus permitting air to be admitted through the tube 107. The milk can now flow through the tube 115.

For cleaning purposes, a cleaning liquid is introduced through the tube 102. The valves 125 and 118 are closed and the valve 123 is opened so that the cleaning liquid fills the apparatus and all flows through the valve 123 when the unit is full. After an electronically controlled time period, the valves 118 and 125 open thus permitting the apparatus to be emptied. This operation can be carried out several times and is preferably followed by a rinsing operation by the method described below.

The rinsing liquid enters the apparatus through the tube 102, fills the apparatus and flows through the tube 123. After a time period, the valves 118 and 125 are opened, thus permitting the apparatus to be drained.

In a variant, the cleaning liquid enters the apparatus via the tube 102, the valves 125 and 118 being closed and the valve 123 open; the cleaning liquid fills the assembly and then flows through the valve 123. After an electronically controlled time period, the valve 125 is opened, thus permitting the measured portion to be emptied. The valve 125 is closed again, the apparatus filled again and, after a time period, the valves 125 and 118 are opened thus permitting the apparatus to be completely emptied.

This operation is then repeated with the rinsing liquid.

What is claimed is:

1. A device for sampling and measuring the flow rate of a continuously or intermittently circulating liquid in particular a foaming liquid, comprising an inlet and an outlet for the liquid, sampling means connected between said inlet and said outlet for taking a sample of the liquid in proportions which are accurate and constant over time, a container connected to said sampling means for receiving the sample thus taken and electrical means in said container for measuring the volume of the sample directly in the container.

2. A device according to claim 1, wherein the sampling means comprise a chamber into which a liquid is admitted and distributed over a dome-shaped convex surface which constitutes the base of the chamber, means for uniformly distributing the flow of the liquid over the convex surface, at least one substantially vertical opening arranged regularly in the chamber, permitting a constant and given proportion of the liquid to be sampled and opening into the container, and finally at least one opening in the chamber for discharging the liquid which is not sampled into the container.

3. A device according to claim 2, wherein there are three vertical openings arranged at 120° to each other.

4. A device according to claim 1, wherein the sampling means comprise a cylindrical chamber into which the liquid is admitted via an inverted funnel-shaped head and uniformly distributed over a conical surface arranged at a small distance from the head, at least one lateral opening made in the wall of the cylindrical chamber permitting a constant and given proportion of the liquid to be sampled and opening into the container, and finally at least one opening in the chamber for discharging the liquid which is not sampled into the container.

5. A device according to claim 4, comprising at least two lateral openings having an axis substantially parallel to the conical surface and arranged immediately beneath it.

6. A device according to claim 4, wherein the conical surface is axially fixed on elastic return means acting against its sinking into the cylindrical chamber.

7. A device according to claim 4, wherein the elastic means comprise a spring.

8. A device according to claim 4, wherein the cylindrical chamber is surrounded by another cylindrical chamber, the annular space between the two chambers serving to admit a liquid for cleaning the container.

9. A device according to claim 1, wherein the electrical means measure the weight of the liquid column present in the container.

10. A device according to claim 1, wherein the electrical means measure the dielectric constant of the liquid present in the container.

11. A device according to claim 10, wherein the electrical means comprise a central anode extending vertically from the base of the container, the second electrode being constituted by the peripheral wall of the container or by a lining placed thereon.

12. A device according to claim 1, further comprising inlet and outlet circuits connected to said inlet and outlet for the liquid, a circuit for emptying the container and a circuit for rinsing and cleaning.

13. A device according to claim 12, wherein all the circuits are constituted by flexible tubes and are controlled by valves acting directly on these tubes.

14. The use of the device according to claim 1 for fresh milk.

* * * * *